United States Patent [19]
Urban et al.

[11] Patent Number: 6,022,984
[45] Date of Patent: Feb. 8, 2000

[54] EFFICIENT SYNTHESIS OF FURAN SULFONAMIDE COMPOUNDS USEFUL IN THE SYNTHESIS OF NEW IL-1 INHIBITORS

[75] Inventors: Frank J. Urban, Waterford; Vytautas J. Jasys, Griswold, both of Conn.

[73] Assignee: Pfizer Inc., New York, N.Y.

[21] Appl. No.: 09/320,439

[22] Filed: May 26, 1999

Related U.S. Application Data

[60] Provisional application No. 60/094,315, Jul. 27, 1998.
[51] Int. Cl.[7] ........................ C07D 307/46; C07D 307/64
[52] U.S. Cl. ........................... 549/479; 549/486; 549/508
[58] Field of Search .................................. 549/479, 486, 549/508

[56] References Cited

U.S. PATENT DOCUMENTS

| | | | |
|---|---|---|---|
| 4,477,679 | 10/1984 | Petrocine et al. | 549/486 |
| 5,470,991 | 11/1995 | Huber | 549/479 |

FOREIGN PATENT DOCUMENTS

WO 98/32733   7/1998   WIPO .

*Primary Examiner*—Ba K. Trinh
*Attorney, Agent, or Firm*—Peter C. Richardson; Paul H. Ginsburg; Jolene W. Appleman

[57] ABSTRACT

An efficent synthesis of furan sulfonamide compounds of formula

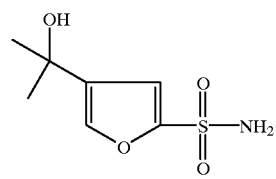

I comprising reacting a compound of formula II with a Grignard reagent in a reaction inert solvent, wherein R' is $(C_1-C_6)$alkyl. The compound of formula II is prepared by reacting a compound of formula III with a compound of formula IV wherein R' is $(C_1-C_6)$alkyl with a chorinating reagent and an acid scaverger in an inert solvent. The invention also includes a novel compound of the formula

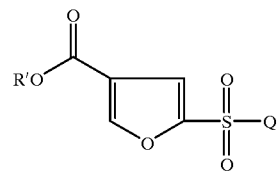

VI wherein R' is $(C_1-C_6)$alkyl and Q is halo, hydroxy or amino.

15 Claims, No Drawings

EFFICIENT SYNTHESIS OF FURAN SULFONAMIDE COMPOUNDS USEFUL IN THE SYNTHESIS OF NEW IL-1 INHIBITORS

This application claims benefit of Provisional Application Ser. No. 60/094,315 filed Jul. 27, 1998.

BACKGROUND OF THE INVENTION

The invention relates to a preparation of furan sulfonamide compounds useful in the synthesis of IL-1 inhibitors. It has now been surprisingly found that by using the electrophilic sulfonation of ($C_1$–$C_6$)alkyl-3 furoate and subsequent functional group manipulation, the process to prepare furan sulfonamide compounds is simplified.

Aryl and hetero substituted urea derivatives are useful in the treatment of inflammation in joints, central nervous system, gastrointestinal tract, endocardium, pericardium, lung, eyes, ears, skin and urogential system. IL-1's status as an important mediator of inflammation is based on many studies demonstrating this cytokine's proinflammatory activity. These effects are manifest as stimulation of cartilage resorption, induction of leukocyte recruitment and the acute phase response, and the production of fever and a shock like state. The changes mediated by IL-1 binding to its receptor include regulation of adhesion molecules and chemokines, stimulation of metalloprotease synthesis, increased synthesis of cyclooxygenase-2 and phospholipase A2 thus increasing prostaglandin production, the induction of nitric oxide synthase thus increasing nitric oxide production and stimulation of IL-6 synthesis resulting in changes in the synthesis of acute phase proteins. Two distinct forms of IL-1 (IL-1 α and IL-1 β) are produced by monocytes and macrophase in response to inflamatory stimuli. This is described in U.S. patent application Ser. No. 60/036,979.

SUMMARY OF THE INVENTION

The present invention relates to a process for preparing a compound of the formula

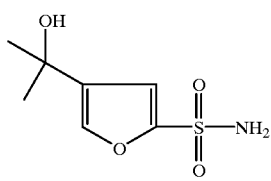

I which comprises reacting with a methyl Grignard reagent in an inert solvent, a compound of the formula II,

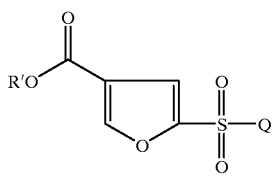

II wherein R' is ($C_1$–$C_6$) alkyl. According to the invention, Compound II may be prepared by reacting a compound of the formula

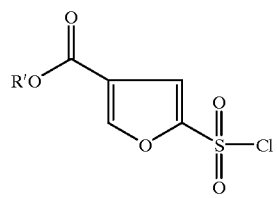

III with an amination reagent in a reaction inert solvent. In one embodiment of the invention to the invention, the compound of Formula III may be prepared by reacting a compound of the formula IV

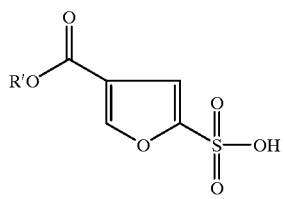

IV with a chlorinating reagent and an acid scavenger in an inert solvent. In another embodiment of the invention compound

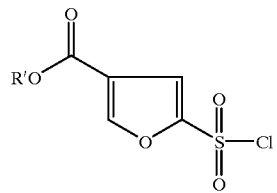

III is prepared by reacting a compound of formula

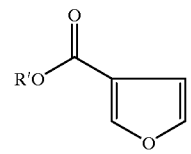

V with an electrophilic sulfonating agent followed by addition of a chlorinating agent and an acid scavenger.

In the process for preparing compound 1, excess Grignard reagent is used. Examples of suitable Grignard reagents are methyl magnesium chloride, methyl magnesium bromide and methyl magnesium iodide. The Grignard reagent is preferably methyl magnesium chloride. The solvent is inert under the reaction conditions and is, preferably, tetrahydrofuran. The aminating agent is an ammonium salt preferably ammonium bicarbonate. The chlorinating agent is chosen from reagents such as phosphorous pentachloride, phosphorous oxy chloride, and thionyl chloride preferably phosphorous pentachloride. The acid scavenger is an organic base preferably pyridine.

The invention also includes a novel compound of the formula

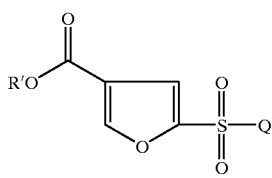

wherein R' is (C$_1$–C$_6$) alkyl and Q is halo, hydroxy or amino. The preferred compounds are those wherein R' is ethyl when Q is chlorine, R' is ethyl when Q is hydroxy and R' is ethyl when Q is amino. In specific embodiments, R' is butyl when Q is chlorine, hydroxy or amino; R' is propyl when Q is chlorine, hydroxy or amino; and R' is hexyl when Q is chlorine, hydroxy or amino. These novel compounds are used in preparation of furansylfonamide compounds useful in the synthesis of IL-1 inhibitors.

DETAILED DESCRIPTION OF THE INVENTION

The new process synthesis is shown in the Reaction Scheme 1 below. R' in the Scheme is as defined above with reference to formula II.

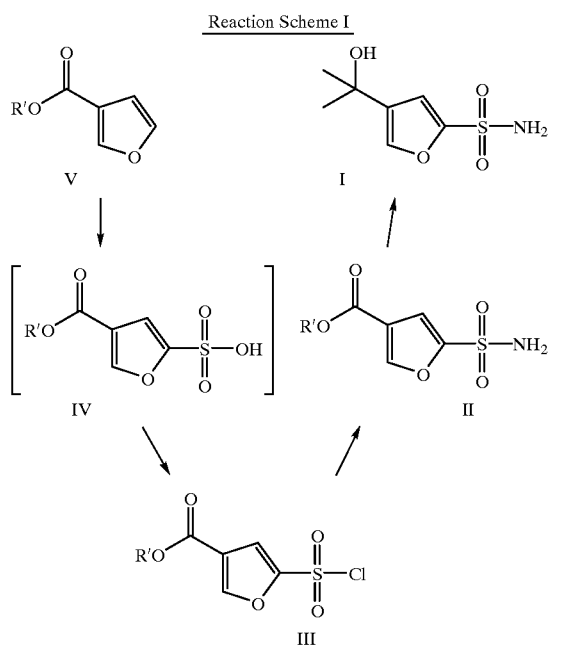

Ester V is treated with an electrophilic sulfonating agent to form sulfonic acid compound IV. Using chlorosulfonic acid and methylene chloride, a portion of the sulfonic acid is crystallized from the reaction mixture. Sulfonic acid compound IV can be isolated as a salt in high purity. Isolated sulfonic acid IV can be converted to sulfonyl chloride compound III with a chlorinating agent and an acid scavenger. In the one pot procedure, Ester V in methylene chloride is treated with chlorosulfonic acid at ice bath temperature and then stirred, for instance for 48 hours, to complete formation of the sulfonic acid compound IV. The reaction was recooled to less then about 0° C., pyridine was added followed by phosphorous pentachloride. After stirring, for instance overnight, at room temperature the sulfonyl chloride compound III can be isolated as an oil. One aspect of the invention is forming III without isolating compound IV.

The primary sulfonamide compound II can be formed under Schotten-Baumann conditions with an aminating agent in aqueous acetone. Compound II may then be treated with excess Grignard reagent in an inert solvent to form Compound I.

Compound I can be used as an intermediate, with an isocyanate compound as shown in Reaction Scheme 2, to form sulfonyl urea derivatives that are useful inhibitors of interleukin-Iα and Iβ. R is decribed in U.S. patent application Ser. No. 60/036,979 which is herein incorporated by reference and can be among the following.

4-Chloro-2,6-diisopropyl-phenyl,
1,2,3,5,6,7-Hexahydro-s-indacen4-yl,
1,2,3,5,6,7-Hexahydro4-aza-s-indacen-8-yl,
8-Chloro-1,2,3,5,6,7-hexahydro-s-indacen4-yl,
8-Fluoro-1,2,3,5,6,7-hexahydro-s-indacen4-yl,
4-Fluoro-2,6-diisopropyl-phenyl, and
2,6-Diisopropyl-phenyl.

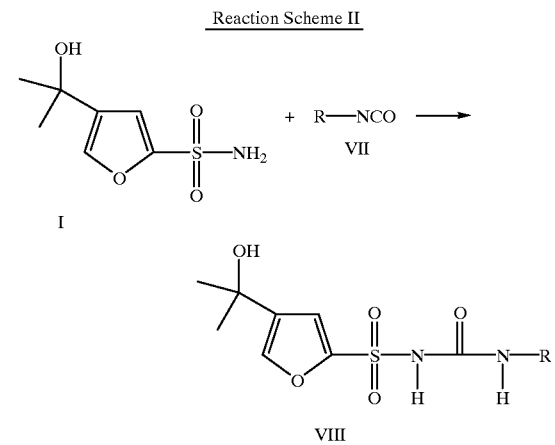

The coupling of isocyanate VII with sulfonamide I requires the presence of a base to deprotonate the sulfonamide. Sodium methoxide and triethylamine can be used in an organic solvent such as tetrahydrofuran or isopropyl alcohol, preferably tetrahydrofuran.

An alternative to the isocyanate process is based on a process where di-t-butyl dicarborate and catalytic dimethylaminopyridine was used to prepare sterically hindered phenylisocyanates in situ. This is shown in Example VII below.

These useful inhibitors VIII of interleukin-1α and interleukin-1β can be administered in a wide variety of dosage forms. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpurrolidine, sucrose, gelation and acacia. Additionally, lubricating agents such as magnesium stearate, sodium lauryl sulfate and talc are often very useful for tabletting purpose. Solid compositions of a similar type may also be employed as filters in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient in usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The present invention is illustrated by the following examples, but it is not limited to the details thereof.

EXAMPLE I
Ethyl 2-(chlorosulfonyl)-4-furoate:

In a four necked one liter flask with mechanical stirring and a nitrogen atmosphere was placed ethyl 3-furoate (50 g, 0.357 moles) and methylene chloride (500 ml). This was cooled to $-10°$ C. and chlorosulfonic acid (24.92 ml, 0.375 moles) was added dropwise over five minutes. The temperature rose to $-6°$ C. The cooling bath was removed and the reaction was allowed to warm slowly to room temperature. The reaction was stirred for 72 hours at which time it consisted of a green solution with a white solid slurry. This was cooled to $-10°$ C. and pyridine (31.7 ml, 0.393 moles) was added dropwise. This caused an exotherm which was controlled by the rate of addition with the temperature below $0°$ C. After this addition, the reaction was a thick slurry. After cooling to $-8°$ C., phosphorous pentachloride ($PCl_5$) (81.74 g, 0.393 moles) was added in 15 g portions over a ten minute period. After stirring for 30 minutes cold, the bath was removed and the reaction was allowed to warm to room temperature. The mixture was stirred overnight.

The reaction mixture was transferred to an addition funnel and added dropwise to water(IL) with stirring at room temperature. During the addition, the temperature rose to $38°$ C. due to the hydrolysis of ($POCl_3$). The addition took 1.5 hours and the mixture was stirred for 45 minutes to assure complete hydrolysis. The layers were separated and the aqueous layer was extracted with methylene chloride (75 ml). The combined organics were washed with water and dried over sodium sulfate. The solution was filtered and evaporated in vacuo to provide the sulfonyl chloride as an oil, 67.8 g, 80% yield. This was suitable as is for use in the next reaction. $^1$HNMR of Ethyl 2-(chlorosulfonyl)-4-furoate ($CDCl_3$, 400 MHZ) δ 8.21 (s, 1), 7.59 (s, 1), 4.35 (q, 2), 1.36 (t, 3), $^{13}$CMR ($CDCl_3$, 400 MHZ) δ 160.5, 151.4, 150. 118.1, 61.7, 14.2.

EXAMPLE II
Ethyl 4-furoate-2-sulfonic acid:

Ethyl 3-furoate (13.5 ml, 0.1 moles) was dissolved in methylene chloride (150 ml) and stirred under nitrogen while being cooled to $-100°$ C. Chlorosulfonic acid (8.3 ml, 0.125 moles) in methylene chloride (25 ml) was added dropwise over 15 minutes. The reaction was warmed to room temperature and stirred overnight. The precipitated, white solid was collected under nitrogen and washed with fresh methylene chloride. This was transferred rapidly to a round bottom flask (the material was hygroscopic) and dried under high vacuum. The yield of hygroscopic white solid was 14.1 g, 64%.

When this material was dissolved in ethyl acetate and dried over sodium sulfate, the sodium salt was isolated as a white solid, mp $220°$ C. (sinters) $245-248°$ C.(dec.) IR (DRIFTS) 3507, 3459, 3155,3127,1731, 1712, 1262, 1231, 1205 $CM^{-1}$). $^1$HMR (D20, 300MHZ) δ 88.19 (s, 1), 7.10 (s, 1), 4.27 (q, 2), 1.30 (t,3). $^{13}$CMR ($D_2O$, 300 MHZ) δ164.4, 152.9, 149.8, 119.6, 110.5, 62.2, 13.4. Analysis Calcd for $C_7H_7O_6SNa$ 0.5 H2O: C, 33.46; H, 3.21; S, 12.76; Na, 9.15. Found: C, 33.77; H, 3.00; Na, 8.97; S, 12.49.

EXAMPLE III

Ethyl 4-furoate-2-sulfonic acid (0.5 g, 2.77 mmoles) was added to (4 ml) pyridine under nitrogen. The sulfonic acid dissolved and then a precipitate formed. The slurry was diluted with ether (18 ml) and stirred. The solid salt was collected, washed with ether and dried. The yield of the pyridinium salt was 0.6 g, 91%, mp $145-146°$ C. IR (DRIFTS) 1726, 1289,1259,1198,1170, 1134,1028 $CM^{-1}$, $^1$HMR ($D_2O$, 300 MHz) δ 8.70 (d, 2), 8.54 (t, 1), 8.11 (s, 1), 7.99 (t, 2), 6.99 (s, 1), 4.20 (q, 2), 1.23 (t, 3). $^{13}$CMR ($D_2O$, 400 Mhz) δ 167.0, 156.0, 152.4, 150.0, 143.9, 130.3, 122.3, 113.1, 64.9, 16.2.

Analysis Calcd for $C_{12}H_{13}NO_6S$: C, 48.15 H, 4.38; N, 4.68; S, 10.71. Found: C, 48.07; H, 4.33; N, 4.70; S, 10.71.

EXAMPLE IV
Ethyl 2-(sulfonamide)-4-furoate:

Ammonium bicarbonate (89.93 g, 1.137 moles) was dissolved in water (1.5 L). This caused the temperature to fall to $17.5°$ C. This was stirred while a solution of sulfonyl chloride (67.8 g, 0.284 moles) in acetone (500 ml) was added dropwise over 16 minutes. During the addition, the temperature rose to $25°$ C. After 65 minutes, thin layer chromatography (tlc) indicated that the reaction was complete (silica gel, 4:1 hexanes: ethyl acetate). Ethyl acetate (500 ml) was added and the pH was lowered to 2.0 with conc. hydrochloric acid (HCl) added dropwise (appr. 53 ml). The layers were separated and the aqueous layer was saturated with sodium chloride (NaCl) and extracted with ethyl acetate. The combined organics were washed with brine and dried over sodium sulfate. The extract was concentrated to about 175 ml and passed through a pad of silica gel which was washed thoroughly with ethyl acetate (final volume 650 ml). The ethyl acetate was removed in vacuo and the residue was taken up in hot ethyl acetate (150 ml) and filtered to remove a haze. This was concentrated to ca. 100 ml and hexanes (250 ml) was added dropwise. The resulting slurry was stirred for 30 minutes, then collected and washed with hexanes/ethyl acetate (4:1). The sulfonamide was air dried. 39.9 g, 64% yield. mp $131-132.5°$ C. IR (DRIFTS) 3340, 3261, 3150, 1697, 1579, 1561, 1364, 1219, 1195 $cm^{-1}$. $^1$HNMR (DMSO-$d_6$, 300 MHz) δ 8.62 (s, 1), 7.94 (s, 2, $NH_2$), 4.25 (q, 2), 1.27 (t, 3). $^{13}$CMR (DMSO-$d_6$, 300 MHz) δ 161.7, 153.9, 150.8, 120.0, 112.0, 61.2, 14.5.

Analysis Calcd for $C_7H_9NO_5S$: C, 38.35; H, 4.14; N, 6.39; S, 14.62. Found: C, 38.42; H, 4.08; N, 6.31; S, 14.70.

EXAMPLE V 4-(1-Hydroxy-1-methyl-ethyl)-furan-2-sulfonamide:

The sulfonamide ester of Example IV (25 g, 0.114 moles) was dissolved in dry tetrahydrofuran (1 L) under nitrogen. The solution was cooled to −10° C. and stirred while methyl magnesium chloride (171 ml, 3 M in tetrahydrofuran) was added dropwise over 5 minutes to give a clear solution. The cooling bath was removed and the reaction allowed to warm to room temperature. During the warm-up the reaction mixture thickened and then became more fluid. After six hours TLC showed that reaction was complete. The reaction was cooled to −5° C. and treated with a solution of ammonium chloride (137.4 g in 700 ml of water). The initial quench caused some exotherm and gas emission during the first 50 ml. The remaining solution was added quickly. After the quench was complete, a clear solution resulted. Ethyl acetate (500 ml) was added and the layers were separated. The aqueous layer was extracted a second time with ethyl acetate (500 ml). The combined organics were washed with brine and dried over sodium sulfate. The solution was filtered and concentrated to low volume. Isopropyl ether (IPE) was added and the solution was concentrated again. During the process, the product was an oil, then solidified. More IPE was added and the slurry was stirred 3 hours. The solid was collected and the filtrate was evaporated to a solid. The solid from the filtrate was triturated with methylene chloride to provide more of the desired product which was combined with the IPE solid and triturated with methylene chloride to afford the sulfonamide alcohol 4-(1-hydroxyl-1-methyl-ethyl-)furan-2-sulfonamide as a solid, 19.98 g, 85% yield. mp 92 (sintered) 99.5–101.5° C. $^1$HNMR (DMSO-$d_6$, 300 Mhz) δ 151.7, 140.3, 136.6, 112.1, 66.6, 31.0.

Analysis Calcd for $C_7H_{11}NO_4S$: C, 40.96; H, 5.40; N, 6.82; S, 15.62. Found: C, 40.73; H, 5.14; N, 6.82; S, 15.53.

4-Acetyl-furan-2-sulfonamide:

From the filtrates of this reaction were isolated small amounts of 4-acetyl-furan-2-sulfonamide as a by product. mp 135–6° C. IR (DRIFTS) 333, 3228, 3144, 1671, 1572, 1355, 1177, 1129 cm$^{-1}$. IHNMR (DMSO-$d_6$, 300 MHz) δ 8.77 (s, 1) 7.93 (s, 2), 7.13 (s, 1), 2.44 (s, 3). $^{13}$CMR (DMSO-$d_6$, 400 MHz) δ 192.3, 151.5, 128.2, 110.8, 28.3.

Analysis Calcd for $C_6H_7NO_4S$: C, 38.09; H, 3.73; N, 7.40: S. 16.95. Found: C, 38.30; H, 3.63; N, 7.36; S, 16.94.

EXAMPLE VI

Sodium salt of 1-(1,2,3,5,6,7-Hexahydro-s-indacen-4-yl)-3-[4-(1-hydroxy-1-methyl-ethyl)-furan-2-sulfonyll]-urea;

The sulfonamide (5 g, 0.0244 mole) was dissolved in tetrahydrofuran (THF) (50 ml) under nitrogen atmosphere. Solid sodium methoxide (1.32 g, 0.0244 mole) was added in one portion. This caused a suspension to form and the color turned to light brown (a small amount of an oily solid is sometimes seen at this point). This mixture was stirred for several hours. The isocyanate (4.77 g, 0.0244 mole) was added as an neat oil. The sodium salt suspension mostly went into solution as the isocyanate was added and a new precipitate formed. After thirty minutes, the reaction still contained a little gummy solids from the sodium methoxide addition. The reaction mixture was heated to reflux for four hours, was cooled to room temperature and the crude sodium salt of substituted sulfonyl urea derivatives of U.S. patent application Ser. No. 60/036,979 was collected and washed with fresh thf. The solids were dried under nitrogen and then under high vacuum. The crude weight was 10.66 g,>100%. NMR showed this was the thf solvate.

The crude sodium salt (5 g, 0.0106 mole) was dissolved in hot isopropanol (100 ml). The solution was filtered through celite and the celite cake was washed with hot isopropanol (2×40 ml). The filtrate was concentrated to 30–35 ml and the solids which precipitated were granulated for 30 minutes at RT, then cooled in an ice water bath. The solids were collected and washed with cold isopropanol. After drying in vacuo, the solids weighed 4.9 g. NMR in $D_2O$ gave a clear solution and showed the presence of the isopropanol solvate.

EXAMPLE VII

Alternative preparation of sodium salt of 1-(1,2,3,5,6,7-Hexahydro-s-indacen4-yl)-3-[4-(1-hydroxy-1-methyl-ethyl)-furan-2-sulfonyl]-urea;

A 500 ml three necked flask was equipped with a magnetic stirrer, a thermometer, and two addition funnels. To the flask under a nitrogen atmosphere was added dry acetonitrile (100 ml), di-t-butyl dicarbonate (30.52 g, 0.14 mole). A solution of dimethylaminopyridine (1.83 g, 0.015 mole) in acetonitrile (25 ml) was added over 3.5 minutes. A slight exotherm of 2 degrees was seen. After stirring for two minutes, a solution of 4-amino-s-hydrindacene (17.1 g, 0.0988 mole) in acetonitrile (100 ml) was added over six minutes. After the addition was complete, the reaction mixture was stirred at room temperature (RT) for 25 minutes. This mixture was added to a slurry of the preformed sodium salt of 4-(1-Hydroxy-1-methyl-ethyl)-furan-2-sulfonamide (23.3 g, 0.098 mole; prepared by addition of one equiv. of sodium methoide to the sulfonamide in methanol solution followed by evaporation) in acetontrile (50 ml). The intiial reaction flask was washed with 2×40 of acetontrile to aid the complete transfer. The combined reaction mixture was stirred at RT overnight. The reaction mixture was heated to a gentle reflux for 1.5 hours to help insure complete reaction. The reaction slurry was cooled to room temperature (RT) and the solids collected and washed with acetonitrile and dried in vacuo to give 30.4 g of crude sodium salt. The sodium salt was triturated with ethyl acetate and recovered by filtration.

The sodium salt (10.25 g, 0.02213 mole, corrected for ethyl acetate content) was dissolved in water (150 ml) and treated with a small amount of Darco. The solution was filtered through a millipore filter. The aqueous filtrate was acidified with 2N Hcl to precipitate the free sulfonylurea. The product was collected by filtration, washed with water and dried in dried. The yield was 8.33 g, 81%.

We claim:

1. A process for preparing a compound of formula

I

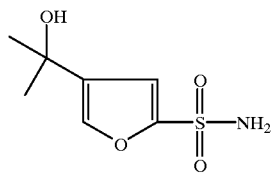

comprising reacting a compound of formula

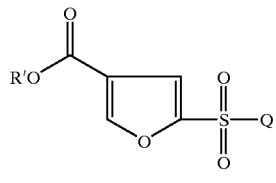

VI wherein R' is ($C_1$ to $C_6$)alkyl with a methyl Grignard reagent in a reaction inert solvent.

2. The process according to claim 1 wherein greater than about 3 equivalents of the Grignard reagent are used.

3. The process according to claim 1 wherein the Grignard reagent is methyl magnesium chloride.

4. The process according to claim 1 wherein the solvent is tetrahydrofuran.

5. The process according to claim 1 wherein said compound of formula 11 is prepared by reacting a compound of formula

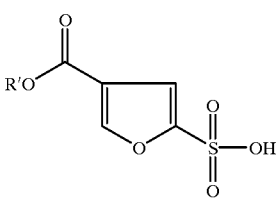

III wherein R' is ($C_1$ to C6)alkyl with an aminating reagent in a reaction inert solvent.

6. The process according to claim 5 wherein the aminating agent is ammonium bicarbonate.

7. The process according to claim 5 wherein said compound of formula III is prepared by reacting a compound of the formula

IV wherein R' is ($C_1$–$C_6$) alkyl, with a chlorinating reagent and an acid scaveger an inert solvent.

8. The process according to claim 7 wherein said chlorinating agent is phosphorous pentachloride.

9. The process according to claim 7 wherein said acid scavenger is pyridine.

10. A process for preparing a compound of formula

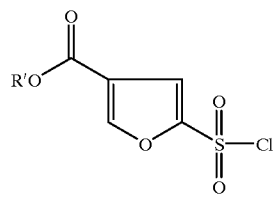

III comprising reacting a compound of formula

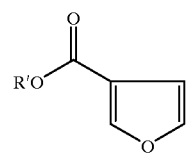

V with an electrophilic sulfonating agent and subsequently with a chlorinating agent and an acid scavenger.

11. The process according to claim 10, wherein the electrophilic sulfonating agent is chlorosulfonic acid in methylene chloride, the chlorinating agent is phosphorous pentachloride and the acid scavenger is pyridine.

12. A compound of the formula

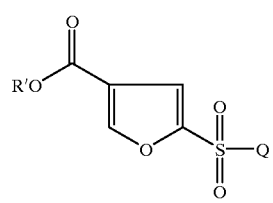

VI wherein R' is ($C_1$–C6) alkyl and Q is halo, hydroxy or amino.

13. A compound according to claim 12 wherein R' is ethyl and Q is Chlorine.

14. A compound according to claim 12 wherein R' is ethyl and Q is OH.

15. A compound according to claim 12 wherein R' is ethyl and Q is $NH_2$.

* * * * *